US006271269B1

(12) United States Patent
Chane-Ching et al.

(10) Patent No.: US 6,271,269 B1
(45) Date of Patent: *Aug. 7, 2001

(54) ORGANIC COLLOIDAL DISPERSIONS OF ACIDIC METAL VALUES

(75) Inventors: Jean-Yves Chane-Ching; Frederic Fabre; Christian Herviou, all of Paris (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/173,485

(22) Filed: Dec. 27, 1993

Related U.S. Application Data

(63) Continuation of application No. 07/832,830, filed on Feb. 5, 1992, now abandoned, which is a continuation of application No. 07/451,772, filed on Dec. 18, 1989, now abandoned, which is a division of application No. 07/316,430, filed on Feb. 27, 1989, now abandoned, which is a continuation of application No. 06/876,635, filed on Jun. 20, 1986, now abandoned.

(30) Foreign Application Priority Data

Jun. 20, 1985 (FR) .................................................. 85 09373

(51) Int. Cl.$^7$ ..................................................... B01J 13/00
(52) U.S. Cl. ............................................................. 516/33
(58) Field of Search ................................ 252/309, 313.1; 516/33

(56) References Cited

U.S. PATENT DOCUMENTS

| | | | | |
|---|---|---|---|---|
| 2,285,477 | * | 6/1942 | White | 516/33 |
| 3,312,630 | * | 4/1967 | Vanik et al. | 252/309 |
| 3,480,555 | * | 11/1969 | Jackson et al. | 252/309 |
| 3,625,856 | * | 12/1971 | Scheafer et al. | 516/33 |
| 3,676,362 | * | 7/1972 | Yates | 252/309 |
| 3,718,584 | * | 2/1973 | Beste et al. | 252/309 |
| 3,888,788 | * | 6/1975 | Yates | 252/309 |
| 4,545,923 | * | 10/1985 | Gradeff et al. | 252/309 |
| 4,770,812 | * | 9/1988 | Watanabe et al. | 252/309 |
| 5,015,452 | * | 5/1991 | Matijevic | 423/263 |
| 5,376,305 | * | 12/1994 | Chane-Ching et al. | 516/89 |

OTHER PUBLICATIONS

Hawley, *The Condensed Chemical Dictionary*, 9$^{th}$ Ed., p 830, Van Nostrand Rienhold Company (1977) New York.*

* cited by examiner

*Primary Examiner*—Edward A. Miller
(74) *Attorney, Agent, or Firm*—Burns, Doane, Swecker & Mathis, L.L.P.

(57) ABSTRACT

Storage-stable sols are comprised of a colloidal dispersion of at least one compound of an acidic metal cation, $M^{n+}$, for example, cerium (IV) and/or iron (III), in an organic phase which comprises an organic liquid medium and an organic acid. The title sols are conveniently prepared via the phase transfer of colloidal particulates from a counterpart aqueous colloidal dispersion.

20 Claims, No Drawings

ORGANIC COLLOIDAL DISPERSIONS OF ACIDIC METAL VALUES

CROSS REFERENCE TO RELATED APPLICATIONS

This application is a continuation of application Ser. No. 07/832,830, filed Feb. 5, 1992, now abandoned, which is a continuation of application Ser. No. 07/451,772, filed Dec. 18, 1989, now abandoned, which is a division of application Ser. No. 07/316,430, filed Feb. 27, 1989, now abandoned, which is a continuation of application Ser. No. 06/876,635, filed Jun. 20, 1986, now abandoned.

Copending applications Ser. Nos. 876,449, 876,681 and 876,800, all filed concurrently the parent application and all assigned to the assignee hereof.

BACKGROUND OF THE INVENTION

1. Field of the Invention

The present invention relates to the preparation of a colloidal dispersion of a metallic cation compound in an organic medium, and, more especially, to the preparation of an organic colloidal dispersion of a compound of a metallic cation which is acidic in character, hereinafter referred to as the cation $M^{n+}$, wherein $n^+$ symbolizes the degree or state of oxidation of the metal and which typically is equal to +3 or +4.

By a "compound of a metallic cation" as utilized herein, there is intended a compound based essentially on the metallic hydroxide thereof and an organic acid.

By a "metallic cation which is acidic in character", or acidic metallic cation, there is intended a cation, the metallic hydroxide of which precipitates at low values of pH, preferably at a pH of less than 4.

Exemplary of such acid cations, representative are the cations of cerium, iron, titanium, zirconium and tin.

In a preferred embodiment of this invention, featured is the preparation of colloidal dispersions of a compound of cerium (IV) and/or a compound of iron (III), in an organic medium.

2. Description of the Prior Art

It is known to this art, from published French Application No. 2,359,192, that certain organic salts of cerium exist which are soluble in solvents and which are characterized in that they have a ratio r between the number of acid equivalents and the number of cerium atoms of from 0.2 to 1; the number of acid equivalents represents the number of acid molecules if the acid used is monofunctional, and it is necessary to double and triple this number in the case of diacids or triacids and, more generally, multiply it by the number of acid functions in the case of a polyacid. The cerium compounds proposed in this manner require a much smaller amount of the acid than the amount theretofore used to obtain the same effect. It is also possible to obtain solutions with higher metal concentrations of up to 500 g/l; the solutions obtained remain fluid and may be manipulated without difficulty while remaining perfectly soluble in hydrocarbon media.

The organic acid may be RCOOH, $RSO_3H$, $ROSO_3H$, $ROPO_3H_2$ or $(RO)_2PO_2H$, with R being a hydrocarbon radical having at least 7 carbon atoms. The organic radical may be a linear or branched chin aliphatic radical or a cyclo-aliphatic radical optionally substituted by an alkyl radical or by an aromatic radical itself optionally substituted by an alkyl radical. The cerium salts of these organic acids may further contain at least one other rare earth metal, e.g., up to 25% of the total content of rare earth metals, including the cerium. It is possible to obtain compositions in the form of solutions in an organic solvent containing more than 200 g cerium per liter of the composition.

The process for the preparation of these cerium salts of an organic acid, or mixtures thereof, consists of reacting, in an organic or a hydroorganic medium, the organic acid and freshly prepared cerium hydroxide $Ce(OH)_3$, in a manner such that the product cerium salts of the organic acid have a ratio r of from 0.2 to 1. The reaction is preferably carried out under heating and the organic medium is preferably a hydrocarbon. After several hours, a part of the water formed during the reaction decants spontaneously. After the reaction, it is possible to assist the separation of the water formed from the reaction medium by adding thereto a third solvent, such as a glycol, an alcohol or an alkyl glycol. The concentration of the solution obtained in this manner is adjusted by adding an appropriate hydrocarbon.

In the examples in this application, the cerium hydroxide $Ce(OH)_3$ is obtained by the precipitation of cerium with ammonia. The precipitate is washed in water until the nitrate ion disappears, and it is then filtered until the nitrate ion disappears, and it is then filtered until it contains less than 15% water. The cerium hydroxide is reacted at 80° C. with 130 g commercial oleic acid in white spirit. After four hours, glycol is added, the separated water eliminated and, subsequently, butyl-glycol added, followed by white spirit to form the final solution.

A process for the preparation of colloidal dispersions of ceric dioxide in inert organic liquids has also been proposed to this art, in published European Application No. 0,097,563, which process consists of:

[1] heating to between 60° C. and 200° C.
  (a) ceric dioxide containing ammonium nitrate in an amount representing from 3% to 14% by weight of the ceric dioxide and a member selected from the group consisting of water, methanol, acetic acid and mixtures thereof in an amount of at least 10 g per mole of $CeO^2$.
  (b) an organic acid having approximately 10 to 40 carbon atoms, in particular oleic acid.
  (c) an organic liquid selected from the group consisting of aliphatic, cycloaliphatic and aromatic hydrocarbons, aliphatic and cycloaliphatic ethers or ketones; and

[2] then eliminating the water, methanol, the acetic acid evolved during heating and separating all of the undissolved solid particles.

A colloidal dispersion of ceric dioxide in an organic medium is obtained, with the ceric dioxide being present in the form of a complex resulting from the physical combination of $CeO_2$ with the organic acid.

It follows from this analysis of the prior art that the processes enabling the preparation of organic sols of ceric dioxide use as their beginning starting material hydrated ceric dioxide, which is most frequently produced by the oxidation and precipitation with a base of a cerium (III) salt, followed by the separation of the resulting precipitate.

SUMMARY OF THE INVENTION

A major object of the present invention is the provision of a novel process for directly preparing a colloidal dispersion of a cerium (IV) salt, while at the same time avoiding the necessity for stages of precipitation and separation of hydrated cerium dioxide.

Regarding organic salts of iron, in French Patent No. 2,172,797 organic salts of iron are described which are soluble in an organic medium and consisting of a complex of an organic or organometallic acid and ferric iron, in which the ratio R of the number of organic acid equivalents to the number of ferric iron atoms is less than 3.

The process for the preparation of said compounds is characterized in that is consists of reacting, with freshly prepared solid ferric hydroxide, one or more of the aforementioned acids, in relative proportions such that the ratio of the number of acid molecules (or equivalents, in the case of diacids or polyacids) to the number of ferric iron atoms is less than 3/1 and preferably between ⅛ and 2; this ferric hydroxide may be prepared in situ in the reaction medium from a ferric salt, or it may be prepared beforehand in a separate stage, but immediately prior to the formation of the soluble organic salt. According to one variant, it is possible to begin with a ferrous salt soluble in water, which is first converted into the ferric salt; it is further possible to precipitate the ferrous hydroxide from an aqueous solution of ferrous salt and then convert this hydroxide into ferric hydroxide by oxidation, for example, by means of atmospheric oxygen, or by an oxidant such as hydrogen peroxide or chlorine.

This invention features a process eliminating the various restrictions of the aforenoted process, i.e.:

(i) The necessity for the preparation of fresh solid ferric hydroxide when preparing an organic salt from the solid hydroxide; and (ii) The necessity for a rigorous control of the process parameters (agitation mixing conditions) in the case of the preparation of the organic salt using a ferric hydroxide prepared in situ.

The present invention also features a process for the separation of an organic colloidal dispersion suitable both for cerium (IV) compounds and for compounds of iron (III), or any other metallic cation which is acidic in character.

Briefly, the present invention features the preparation of a colloidal dispersion of a compound of a metallic cation which is of an acid character, in an organic medium, characterized in that it comprises:

(i) contacting:

(a) an aqueous phase which comprises at least one colloidal dispersion of at least one compound of the said $M^{n+}$ cation in an aqueous medium supersaturated in $OH^-$ ions, obtained by the reaction of an $M^{n+}$ cation with a base, (b) an organic phase comprising an organic acid and a liquid organic medium or solvent; and (ii) subsequently separating the aqueous phase and the organic phase.

DETAILED DESCRIPTION OF THE PREFERRED EMBODIMENTS OF THE INVENTION

More particularly according to the present invention, one characteristic feature thereof is the provision of an organic sol, with this expression intended to designate the dispersion of the compound of the $M^{n+}$ cation in an organic medium, by the transfer of said compound into an organic phase from an aqueous phase comprising the compound of the cation $M^{n+}$ present in colloidal form, in an aqueous medium supersaturated in $OH^-$ ions.

The state or degree of supersaturation is defined as the pH zone wherein the compound of the cation $M^{n+}$ is present in the colloidal form, whereas it would have been expected, in view of the solubility product of the metallic hydroxide, that precipitation of said hydroxide would have occurred. This state of supersaturation is attained when the base is used in such an amount to prepare the $M(OH)_n$ that it constitutes 60 to 95 molar % of the amount of base theoretically required to neutralize the cation $M^{n+}$ present in the reaction medium.

The aqueous sol is defined as the colloidal dispersion of the compound of the cation $M^{n+}$ in the aqueous medium, which is the beginning material in the process of the invention.

In order to carry out the process of the invention in a highly satisfactory manner, it is desirable that the initial aqueous sol satisfy the following requirements:

(i) the proportion of the metal M in the colloidal form should be as high as possible, and preferably greater than or equal to 95%;

(ii) the concentration of the cation $M^{n+}$ in the aqueous sol must be adequate and preferably ranges form 0.1 to 3 moles/liter; and (iii) the aqueous sol must have good thermal stability and must not flocculate at the temperature of the reaction, which is higher than 60° C. and most frequently ranging from 80° to 100° C.

In the first stage of the process, the preparation of at leas tone colloidal dispersion of at least one compound of an $M^{n+}$ cation in an aqueous medium supersaturated in $OH^-$ ions is carried out by reacting an aqueous solution of at least one salt of the cation $M^{n+}$ with a base, under the conditions hereinafter described.

In the process of the invention, an aqueous colloidal dispersion of a compound of a cation $M^{n+}$, a mixture of two or more aqueous colloidal dispersion of different compound of an $M^{n+}$ cation, or an aqueous colloidal dispersion of a compound of different $M^{n+}$ cations, may be used.

One technique for preparing an aqueous colloidal dispersion of a compound of an $M^{n+}$ cation is given below, with $M^{n+}$ representing cerium (IV) or iron (III).

To prepare the aqueous colloidal dispersion of a compound of cerium (IV), an aqueous solution of ceric nitrate or an aqueous solution of ceric-ammonium nitrates may be used. This solution may contain, without imparting detrimental effects, cerium in the cerous state, but it is desirable that it contain at least 85% of cerium (IV).

The solution of the cerium salt is selected such as to be devoid of impurities which may be transferred into the final product. In particular, it is preferable that it be free from covalent anions which are coagulating in nature, such as sulfates, and the like. However, small amounts may be tolerated. For example, said anions may constitute up to 5% by weight of the cerium salt, expressed as $CeO_2$.

The concentration of the solution of the cerium salt advantageously varies from 0.1 to 3 moles per liter. It may be desirable, in view of the productivity of the equipment, to use a concentration solution of the cerium (IV) salt, with a concentration ranging from 1.25 to 2 moles per liter being preferred.

The aqueous solution of the cerium (IV) salt typically has a certain initial acidity and may have a normality of from 0.1 N to 4 N. The concentration in $H^+$ ions is not critical. It is desirable that it range from 0.1 N to 1 N.

The solution of a ceric nitrate obtained via the electrolytic oxidation of a cerous nitrate solution as described in published French Application No. 2,570,087 (No. 84/13641) is a most preferred material.

The basic solution, or base reactant, is advantageously an aqueous solution of ammonium, sodium or potassium hydroxide. Gaseous ammonia may also be used. In a preferred embodiment of the invention, an aqueous ammonia solution is used.

The normality of the basic solution is also not critical according to the invention and may vary over a wide range, for example, from 1 to 11 N, but it is preferable, in order to obtain solutions concentrated in cerium (IV) values, to first use a solution having a concentration of from 5 to 11 N and then a solution diluted, for example, to from 1 to 5 N.

The ratio between the basic solution and the solution of the cerium (IV) salt should be such that the degree fo supersaturation is greater than 3 and less than 4.

The degree of supersaturation r is defined by the following equation:

$$r = (n3-n2)/n1$$

wherein:
 n1 represents the number of moles of Ce (IV) values present in the final colloidal dispersion;
 n2 represents the number of moles of $OH^-$ necessary to neutralize the acidity introduced via the aqueous solution of the cerium (IV) salt; and
 n3 represents the total number of moles of $OH^-$ introduced by the addition of the base.

The degree of supersaturation r reflects the colloidal state of the cerium (IV) values.
 with r=4, the cerium (IV) precipitates in a gelatinous form;
 with r=0, the cerium (IV) is in the ionic form; and
 with o<r<4.0, the cerium (IV) is in the ionic and/or colloidal form.

It has now unexpectedly been determined that the provision of a good dispersion of colloids of the cerium (IV) compound in the organic phase is linked to the colloidal state of the cerium (IV) compound in the aqueous phase.

According to the invention, a degree of supersaturation greater than 3 and less than or equal to 3.8 is advantageously utilized to provide a final concentration in cerium (IV) in the resulting colloidal dispersion of form 0.1 M (or 17 g/l $CeO_2$) to 2 M (or 344 g/l $CeO_2$). Preferably, the degree of supersaturation is greater than or equal to 3.4 and less than or equal to 3.8 to provide a final concentration in cerium (IV) in said dispersion varying from 0.5 M (or 86 g/l $CeO_2$) to 1.2 M (or 206 g/l).

In actual practice, in order to provide a degree of supersaturation r within the aforenoted range for a given concentration of Ce (IV) in the final colloidal dispersion, the concentration of the basic solution is adjusted such that it satisfies the following equation:

$$\{OH^-\} = \frac{(n_1 \cdot r + n_2)\,[Ce(IV)]_f\,[Ce(IV)]_i}{n_1([Ce(IV)]_i - [Ce(IV)]_f)}$$

wherein:
 [$OH^-$] is the concentration in moles/liter of the basic solution:
 [Ce (IV)]$_f$ is the concentration in Ce (IV) in moles/liter of the product colloidal dispersion;
 [Ce (IV)]$_i$ is the concentration in Ce (IV) in moles/liter of the aqueous solution of the cerium (IV) salt; and
 $n_1$ and $n_2$ are determined by conventional analysis of the aqueous solution of the cerium (IV) salt;
  $n_1$ by potentiometric titration with the aid of a solution of ferrous salt, and
  $n_2$ by acid/basic titration after complexing the cerium with the aid of oxalate ions.

It is possible to relate, to a given degree of supersaturation, an amount of base introduced, expressed as a molar percentage of the quantity of base theoretically required for the complete neutralization of the cerium (IV) present in the reaction medium, to obtain $Ce(OH)_4$.

A molar amount of base introduced, greater than 75% and less than 100% of said theoretical amount, corresponds to a degree of supersaturation greater than 3 and less than 4.

Exemplary of the above, it is noted that degrees of supersaturation of 3.5 and 3.8 respectively correspond to molar amounts of the base introduced representing 87.5 and 95% of the theoretical amounts.

A preferred embodiment of the invention comprises provided the degree of supersaturation by controlling the pH of the reaction medium. an aqueous medium is obtained, hereinafter referred to as an "aqueous sol".

It should be noted that the cerium (IV) compound is present in the form of a colloidal dispersion in water, which indicates that said compound is in the form of particulates having colloidal dimensions, but this does not exclude the presence of the Ce (IV) in the ionic form. However, it is preferable that the proportion of cerium in the colloidal form be as high as possible and preferably greater than or equal to 95%.

The cerium (IV) compound in the colloidal state in the aqueous corresponds to the following chemical formula (I):

$$Ce\,(OH)_x\,(NO_3)_{4-x} \qquad (I)$$

wherein x ranges from 0.3 to 0.7.

The aqueous sol obtained has a concentration in cerium (IV) values which is not critical and may range from 0.1 to 2 moles/liter.

The density of the colloids is measured in the colloidal dispersion by determining the molecular weight by the conventional light diffusion method and by correlation with the hydrodynamic diameter defined by the method of quasi-elastic diffusion of light.

The density of the colloids is always less than that of $CeO_2$ (d=7.2). It varies from 3.5 to 6.0 and increases with rising degrees of supersaturation.

The size of the colloids is defined by measuring the hydrodynamic diameter of the colloids, determined by the quasi-elastic diffusion of light according to the method described by Michael L. McConnell in *Analytical Chemistry*, Vol. 53, No. 8, 1007 A (1981); the diameter may vary from 50 to 400 Å.

Concerning the preparation of a colloidal aqueous dispersion of an iron (III) compound, any aqueous solution of a ferric salt may be used, in particular a solution of ferric chloride or nitrate.

The iron salt solution is selected such that it contains no more than 5% of anions which are coagulating in nature.

The concentration of the iron salt solution may vary from 0.1 to 3 moles per liter; a concentration of from 0.5 to 1.5 moles per liter is preferred.

The aqueous solution of the iron salt typically has a certain initial acidity which is not critical; it may have a normality of from 0.01 N to 2 N.

The iron may be introduced into the reaction medium in the ferrous state, and it is oxidized into the ferric state by adding to the reaction mixture an oxidizing agent compatible with the medium. Among the suitable oxidizing agents, especially representative are solutions of perchlorate, chloride, hydrogen peroxide or air, oxygen and ozone. The iron may also be oxidized electrochemically.

Preferably, hydrogen peroxide is used.

The proportion of the oxidizing agent with respect to the ferrous iron to be oxidized may vary over wide limits. It is generally greater than the stoichoimetric amount and preferably is a stoichiometric excess of from 10 to 40%.

The basic solution used is similar to that described above relative to its nature, its concentration and mode of application.

The ratio between the amounts of basic solution and the solution of the iron is such that the degree of supersaturation is greater than 2.2 and less than 2.7.

In a practical manner, in order to provide a certain degree of supersaturation, the concentration of the basic solution may be adjusted according to the equation defined for cerium.

By way of example, it is also possible to obtain a degree of supersaturation of from 2.2 to 2.6 by controlling the pH of the reaction medium at from 1.7 to 2.6, for a final concentration of $Fe^{3+}$ or 0.5 mole/liter.

The reaction between the aqueous solution of the iron salt and the base may be carried out under the conditions described for the preparation of the aqueous colloidal dispersion of the cerium (IV) compound. Preferably, the reaction mixture may be subjected to a heat treatment at a temperature of from 15° C. to 80° C. for from 5 min to 8 hours.

A colloidal dispersion of a compound of iron (III) in an aqueous medium, the colloidal particle sizes of which range from 100 to 700 Å, is obtained.

According to a second embodiment of the invention, two or more aqueous colloidal dispersions of different compounds of the $M^{n+}$ cation are used.

It is thus possible to begin with a colloidal dispersion of a cerium (IV) compound and a colloidal dispersion of an iron (III) compound prepared by two different methods.

The ratio between said dispersions may be such as to provide a mixture containing:

15 to 85% of a cerium (IV) compound expressed as the weight of cerium with respect to the total weight of the metals, and 15 to 85% of an iron (III) compound expressed as the weight of iron with respect to the total weight of the metals.

In another embodiment of the invention, an aqueous colloidal dispersion of a compound of different $M^{n+}$ cations may be used.

An aqueous colloidal dispersion of a mixed metal compound containing different cations which are acidic in nature is prepared.

The process of preparing said dispersion includes reacting an aqueous solution of at least tow salts of a metal M with a base, in an amount such that it represents 60 to 95% in moles of the amount of base theoretically required for the complete neutralization of the $M^{n+}$ cations present in the reaction medium, to obtain $M(OH)_n$.

The characteristics of the reagents and the conditions of their application correspond to those described above.

At least two metals M in the same form, and preferably in the form of the nitrates thereof, are used.

The operational procedure may differ depending on whether the metals are or are not in the form of an aqueous solution.

The aqueous solutions of at least two salts of the metals M may be mixed together and then the base added thereto.

It is also possible to introduce one or more salts of the metal M in the solid form (anhydrous or hydrated) into the aqueous solution of the salt of at least one other metal M and then add the base.

A colloidal dispersion of an intermetallic compound in an aqueous medium is obtained, said dispersion comprising colloidal particulates having hydrodynamic diameters varying from 50 to 2000 Å.

Consistent herewith, an aqueous phase comprising the aforedescribed colloidal dispersion or dispersions is contacted with an organic phase containing an organic liquid medium or solvent and an organic acid.

The liquid organic medium used according to the invention may be an inert aliphatic or cycloaliphatic hydrocarbon, or mixture thereof, such as, for example, gasoline or petroleum, mineral ethers or petroleum ethers which may also contain aromatic components. Exemplary are hexane, heptane, octane, nonane, decane, cyclohexane, cyclopentane, cycloheptane and liquid naphthenes. Aromatic solvents, such as benzene, toluene, ethyl benzene and the xylene are also suitable, as are the petroleum cuts of the Solvesso type (trademark of EXXON Co.), in particular Solvesso 100, which essentially are a mixture of methylethyl and trimethylbenzene and Solvesso 150, which comprises a mixture of alkylbenzenes and particularly dimethylethylbenzene and tetramethylbenzene.

Chlorinated hydrocarbons, such as chloro- or dichlorobenzene and chlorotoluene, together with aliphatic and cycloaliphatic ethers, such as diisopropyl ether, dibutyl ether and aliphatic and cycloaliphatic ketones, diisobutylketone, mesityl oxide, may also be used.

The liquid organic or solvent system is selected by taking into account the solubilizing organic acid used, the heating temperature and the final application of the solution or colloidal dispersion. In certain cases, it is preferable to use a mixture of solvents. The quantity of the liquid or solvent determines the final concentration. It is more economical and convenient to prepare concentrated dispersions which may be diluted later during their application. For this reason, the amount of the solvent is not critical.

It may be advantageous to add to the organic phase a promoting agent with the function of accelerating the transfer of colloids from the aqueous phase into the organic phase and to improve the stability of the organic sols obtained. Exemplary of such promoters, compounds with an alcoholic function and in particular linear or branched chain aliphatic alcohols having 6 to 12 carbon atoms are representative.

As specific examples, 2-ethyl hexanol, decanol, dodecanol, or mixtures thereof, are representative.

The amount of said agent in the organic phase is not critical and may vary over wide limits.

However, an amount of from 2 to 15% by weight is typically used.

Concerning the organic acid, aliphatic carboxylic acids, aliphatic sulfonic acids, aliphatic phosphonic acids, alkylarylsulfonic acids and alkylarylphosphonic acids having approximately 10 to 40 carbon atoms may be used; they may be natural or synthetic and may be employed either by themselves or in their mixtures. Exemplary thereof, representative are tall oil fatty acids, coconut oil, soybean oil, tallow, linseed oil, oleic acid, linoleic acid, steric acid, isostearic acid, pelargonic acid, capric acid, lauric acid, myristic acid, pelargonic acid, capric acid, lauric acid, myristic acid, dodecylbenzenesulfonic acid, 2-ethyl-hexoic acid, naphthenic acid, hexoic acid, toluene-sulfonic acid, toluene-phosphonic acid, lauryl-sulfonic acid, laurylphosphonic acid, palmityl-sulfonic acid and plamitylphosphonic acid. Preferably, oleic acid or an alkylarylsulfonic acid is used.

The amount of the organic acid used, expressed as the number of moles of the acid per mole of the compound of an $M^{n+}$ cation, may vary over a wide range of from 0.25 to 1 mole per mole of $M_2O_n$. The upper limit is not critical, but it is not necessary to use too much acid. The organic acid is used in a amount of 0.25 to 0.8 mole per mole of $M_2O_n$.

In the organic phase, the ratio between the organic solvent and the organic acid is not critical. The weight ratio of the organic solvent to the organic acid preferably ranges from 0.3 to 2.0.

The order of the introduction of the different reagents is immaterial. The mixture may be carried out simultaneously of the aqueous colloidal dispersion, the organic acid, the organic solvent and optionally the promoting agent, which form the organic phase.

The temperature of the reaction medium preferably ranges form 60° to 150° C.

In certain cases, in view of the volatility of the organic solvent, its vapors must be condensed by cooling to a temperature less than its boiling point.

Preferably, the operation is carried out at a temperature of from 80° to 100° C.

The reaction mixture is maintained under agitation during the entire duration of heating, which may be less than an hour to about 24 hours, preferably from 2 to 6 hours.

Upon completion of this heating period, the heating is discontinued. The presence of two phases is noted: an organic phase containing, in dispersion, the metal-organic acid complex, and an aqueous phase containing the basic salt.

The organic and the aqueous phases are then separated by conventional separation methods: decantation, centrifuging, and the like.

According to the present invention, organic colloidal dispersions of a compound of a metal $M^{n+}$ cation are obtained, containing one or more $M^{n+}$ cations, the colloidal size of which may be highly variable by manipulating certain parameters, in particular the hydrodynamic diameter of the initial aqueous colloidal dispersions or the molar ratio organic acid/$M^{n+}$ compound.

Generally, the hydrodynamic diameter of the colloids obtained, determined by the quasi-elastic diffusion of light, ranges from 80 Å to 1,200 Å.

For certain applications, it is possible to use the reaction mixture as is, but on occasion it is desirable to eliminate the water, which may constitute 1 to 3% by weight of the organic phase. For this purpose, means well known to this art are employed, for example, the addition of a third solvent inert with respect to the $M^{n+}$ compound, having a boiling point of preferably lower than 100° C. and forming an azeotrope with the water, then distilling the resulting azeotrope. As suitable solvents, aliphatic hydrocarbons, such as hexane, heptane, cycloaliphatic and aromatic hydrocarbons, alcohols such as, for example, ethylene glycol, diethylene glycol, etc., are exemplary.

The invention is particularly appropriate for the preparation of organic colloidal dispersions of cerium (IV) compounds.

The sols obtained according to the invention have a concentration in the cerium (IV) compound that may be very high, up to from 3.5 M to 4 M of $CeO_2$.

It is found that the yield of the extraction of cerium in the organic phase is very good, up to 90 to 95%.

By the quasi-elastic diffusion of light, the presence of colloids having a hydrodynamic diameter varying with the conditions of preparation, is determined, and is on the order of 60 to 500 Å.

After the insolubilization of the colloids by the extraction of the organic solvent in acetone, a powder is recovered, the elementary analysis of which shows a molar ratio of organic acid/cerium varying from 0.2 and 0.6, depending on the mode of preparation.

The organic sols prepared in this manner have excellent stability. No settling is observed after several months. This invention also features the use of the product organic sols as drying agents in the paint and varnish industries, as they accelerate the drying of unsaturated oils, and as combustion additives in liquid fuels for energy generators, such as internal combustion engines, oil burners or jet propellants.

In order to further illustrate the present invention and the advantages thereof, the following specific examples are given, it being understood that same are intended only as illustrative and in nowise limitative.

Examples 1 to 5 relate to the preparation of an organic sol of cerium (IV) in different organic media.

Examples 6 and 7 relate to providing a mixed organic sol of cerium (IV) and iron (III).

EXAMPLE 1

(1) Preparation of an aqueous colloidal dispersion of a cerium (IV) compound:

Into a 6 liter three-necked flask equipped with a thermometer, agitating means, and a system for the introduction of the reagents (metering pump), 1000 cm³ of a ceric nitrate solution were introduced at ambient temperature, containing 1.64 moles/liter of cerium (IV), 0.07 mole/liter cerium (III) and having a free acidity of 0.42 N (obtained by electrolysis according to French Application No. 2,570,087).

To this solution, under agitation and at ambient temperature, 545 cm³ of an 11.3 N ammonia solution were gradually added at a rate of 100 cm³/hr.

An aqueous colloidal dispersion of a cerium (IV) compound was obtained, having a concentration, expressed as $CeO_2$, of 183 g/l and a pH of 1.3.

The size of the colloids was determined by the quasi-elastic diffusion of light according to the method described by Michael L. McConnel in *Analytical Chemistry*, Vol. 53, No. 8,1007 A (1981). The average hydrodynamic diameter of the colloids was on the order of 80 Å.

(2) Preparation of an organic sol of a cerium (IV) compound:

Into a 250 cm³ Erlenmeyer flask equipped with a magnetic agitator device, surmounted by a condenser and equipped with a heating device having temperature controls, there were introduced 100 g of the aqueous sol prepared according to step (1) and an organic phase containing 13.6 cm³ oleic acid.

The mixture was agitated and heated to 90° C., which temperature was maintained for 4 hours under agitation.

Upon completion of the reaction, the formation of a brown phase characteristic of an organic colloidal dispersion of ceric hydroxide was observed.

The separation of the organic phase and the aqueous phase was carried out by simple decantation.

A $CeO_2$ content on the order of 517 g/l was determined in the organic sol obtained by a method consisting of calcining at 1000° C. a sample of the organic sol, then weighing the solid residue obtained.

The presence of colloids having a hydrocynamic diameter on the order of 109 Å was demonstrated by the quasi-elastic diffusion of light.

Following the insolubilization of the colloids by the extraction of the organic solvent in acetone, a brownish-chestnut colored powder was recovered. The elementary analysis of the powder showed a molar ratio of oleic acid/$CeO_2$ on the order of 0.57; the $CeO_2$ was determined by weighing, after calcination, and the oleic acid by infrared spectrometry of the gaseous carbon dioxide released during calcination.

EXAMPLE 2

Into the apparatus described in Example 1, 100 cm$^3$ of the aqueous sol prepared in step (1) was contacted with an organic phase containing 20.11 cm$^3$ of an aromatic hydrocarbon marketed under the trademark SOLVESSO 150 and 16.8 cm$^3$ oleic acid.

The mixture was agitated and heated to 90° C.; this temperature was maintained for 4 hours under agitation.

After 2 hours, the formation of a brown phase characteristic of the organic colloidal dispersion of ceric hydroxide was observed.

After the separation of the two phases by decantation, an azeotrope entrainment of water in hexane was effected.

A CeO$_2$ content on the order of 450 g/l in the product organic sol was determined.

The hydrodynamic diameter of the colloids was 150 Å, as determined by quasi-elastic light diffusion.

The chemical analysis performed on the powder after the insolubilization of the colloids by the extraction of the organic solvent in acetone showed a molar ratio of oleic acid/CeO$_2$ of 0.5.

EXAMPLE 3

100 cm$^3$ of the aqueous sol prepared according to Example 1, step (1), were contacted with an organic phase containing 32 cm$^3$ of an aromatic hydrocarbon marketed under the trademark SOLVESSO 150 and 8.4 cm$^3$ oleic acid.

The mixture was agitated and heated to 90° C.; this temperature was maintained for 24 hours under agitation.

After 12 hours, the formation of a brown phase characteristic of the organic colloidal dispersion of ceric hydroxide was observed.

After the separation of the two phases by decantation, an azeotrope entrainment of the water in hexane was effected.

A CeO$_2$ content on the order of 420 g/l in the product organic sol was determined.

The hydrodynamic diameter of the colloids of the organic sol was 500 Å, as determined by the quasi-elastic diffusion of light.

Chemical analysis performed on the powder after insolubilization of the colloids by the extraction of the organic solvent in acetone showed an oleic acid/CeO$_2$ ratio of 0.31.

EXAMPLE 4

Into the apparatus of the above-described type, 100 cm$^3$ of an aqueous colloidal dispersion of a cerium (IV) compound prepared by the method described in Example 1, step (1) containing 0.7 mole/liter of cerium (IV) and having a pH of 1.8, were contacted with an organic phase containing 15 cm$^3$ of an aliphatic solvent marketed under the trademark AMSCO and 10.6 cm$^3$ oleic acid.

The mixture was agitated and heated to 90° C. The temperature was maintained for 4 hours under agitation.

After 3 hours, the formation of a brown phase characteristic of the organic colloidal dispersion of ceric hydroxide was observed.

Following the separation of the two phases by decantation, an azeotropic entrainment of the water in hexane was effected.

A CeO$_2$ content on the order of 300 g/l in the product organic sol was determined.

A hydrodynamic diameter of the colloids of the organic sol on the order of 150 Å was determined by the quasi-elastic diffusion of light.

EXAMPLE 5

Into the apparatus described above, 100 cm$^3$ of an aqueous colloidal dispersion of a cerium (IV) compound prepared as in Example 1, step (1), and containing 0.95 mole/liter of cerium (IV) and having a pH of 1.9, were contacted with an organic phase containing 21.4 cm$^3$ of SOLVESSO 150, 15.2 cm$^3$ oleic acid and 1.1 cm$^3$ 2-ethyl hexanol.

The mixture was agitated and heated to 90° C. This temperature was maintained for 4 hours under agitation.

After the separation of two phases, an entrainment of the water in hexane was effected.

A CeO$_2$ content on the order of 375 g/l CeO$_2$ was determined in the organic sol obtained.

A hydrodynamic diameter on the order of 150 Å of the colloids of the organic sol was determined by the quasi-elastic diffusion of light.

EXAMPLE 6

A colloidal dispersion supersaturated in OH$^-$ ions of ferric nitrate was prepared by adding at ambient temperature 250 cm$^3$ of 2.89 N ammonia at a rate of 100 cm$^3$/hr to 250 cm$^3$ of a ferric nitrate solution FE$^{3+}$=1 M and h$^+$=0.5 N.

After 10 days at ambient temperature, the colloidal solution obtained had a pH of 1.75 and a concentration of 0.5 M in Fe$^{3+}$.

100 cm$^3$ of the aqueous colloidal dispersion supersaturated in OH$^-$ of ferric hydroxide previously synthesized was mixed with 100 cm$^3$ of the aqueous colloidal solution of ceric hydroxide described in Example 1 and this mixture was contacted with 38.46 cm$^3$ oleic acid and 16.5 cm$^3$ of the solvent SOLVESSO 150 at 90° C.

After 24 hours, a brown phase was recovered by decantation and the water was eliminated therefrom by azeotropic entrainment in hexane.

A hydrodynamic diameter of the colloids of the organic sol on the order of 1200 Å was determined by the quasi-elastic diffusion of light.

By calcination at 1000° C. for 2 hours of a wall defined aliquot portion of the organic sol, an oxide content of approximately 300 g/l in the product organic sol was determined.

The cerium and iron content of the colloids of the organic sol was determined by X-ray fluorescence analysis of the solid residue obtained after ultra-centrifugation, drying and calcination at 1000° C.

The molar ratio Fe/Ce determined comparatively with defined Fe/Ce standards was on the order of 0.5.

EXAMPLE 7

A colloidal dispersion supersaturated in OH$^-$ ions of ferric nitrate was prepared by adding, at ambient temperature, 857 cm$^3$ of 6.65 N ammonia at a rate of 100 cm$^3$/hr to 2 liters of a ferric nitrate solution of Fe$^{3+}$=1 M and H$^+$=0.5 N.

The colloidal solution obtained had a pH of 1.75 and a concentration of 0.70 M in Fe$^{3+}$.

100 cm$^3$ of the aqueous colloidal dispersion supersaturated in OH$^-$ of ferric hydroxide previously synthesized were mixed with 100 cm$^3$ of an aqueous colloidal solution of ceric hydroxide (CeO$_2$=120 g/l, pH=1.8) and this mixture was contacted with 21.6 cm$^3$ of oleic acid and 14.5 cm$^3$ of the solvent SOLVESSO 150 at 90° C.

After 24 hours, a brown phase was recovered by decantation and the water was eliminated by azeotropic entrainment in hexane.

A hydrodynamic diameter of the colloids on the order of 900 Å was determined by the quasi-elastic diffusion of light.

By calcination at 1000° C. for 2 hours of an aliquot portion of the organic sol, a content of approximately 300 g/l of oxides was determined in the product organic sol.

X-ray fluorescence analysis of the calcined product performed with respect to standards of a defined Fe/Ce composition showed a molar ratio Fe/Ce on the order of 1.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a storage-stable organic sol comprising:

(i) reacting (a) a base reactant with (b) at least one aqueous solution of a salt of an acidic metal cation $M^{n+}$ to form (c) an aqueous colloidal dispersion of $M^{n+}$ values, in respective amounts of (a) and (b) effective to provide in the aqueous colloidal dispersion (c) a degree of supersaturation r in OH⁻ ions, wherein r is defined by the following equation, $$r = (n3 = n2)/n1$$

wherein n1 is the number of moles of $M^{n+}$ values present in the colloidal dispersion(s), n2 is the number of moles of OH⁻ necessary to neutralize acidity introduced via the aqueous solution(s) of acidic metal cation(s) $M^{n+}$, and n3 is the total number of moles of OH⁻ introduced by the base reactant;

(ii) contacting the resulting aqueous colloidal dispersion of $M^{n+}$ values with (d) an organic phase comprising (d1) an organic liquid medium and (d2) an organic acid, to form (e) an aqueous/organic phase mixture; and (iii) separating mixture (e) into an aqueous phase and a product organic phase.

2. The process as defined by claim 1, wherein at least 95% of metal M in the aqueous colloidal dispersion is in colloidal form.

3. The process as defined by claim 1, said aqueous colloidal dispersion having a concentration in $M^{n+}$ values of from 0.1 to 3 moles/liter.

4. The process as defined by claim 1, said $M^{n+}$ values comprising cerium (III) values and said degree of supersaturation being greater than 3 but less than 4.

5. The process as defined by claim 4, said degree of supersaturation being greater than 3 but less than 3.8.

6. The process as defined by claim 1, said $M^{n+}$ values comprising iron (III) values and said degree of supersaturation being greater than 2.2 but less than 2.7.

7. The process as defined by claim 1, comprising contacting at least two aqueous colloidal dispersions of different $M^{n+}$ compounds with said organic phase.

8. The process as defined by claim 7, comprising contacting and aqueous colloidal dispersion of cerium (IV) values and an aqueous colloidal dispersion of iron (III) values with said organic phase.

9. The process as defined by claim 8, said respective dispersions comprising admixture of 15 to 85% of cerium (IV) values with respect to the total weight of acidic metal values, and 15 to 85% of iron (III) values, also with respect to the total weight of acidic metal values.

10. A process according to claim 1, wherein $M^{n+}$ comprises at least one cation of cerium, iron, titanium, zirconium and tin.

11. A process according to claim 10, wherein $M^{n+}$ comprises a cation of cerium (IV).

12. A process according to claim 10, wherein $M^{n+}$ comprises a cation of iron (III).

13. A process according to claim 10, wherein the hydrodynamic diameter of the colloidal particles in the product organic phase range from 80 to 1200 Å.

14. A process according to claim 10, wherein the hydrodynamic diameter of the colloidal particulates in the product organic phase range form 60 to 500 Å.

15. A process according to claim 11, wherein the concentration in cerium (IV) values is from 3.5 M to 4 M, expressed as $CeO_2$.

16. A process according to claim 10, wherein the ratio between the organic liquid medium (d1) and the organic acid (d2) ranges from 0.3 to 2.0.

17. A process according to claim 10, wherein the organic phase (d) further comprises an aqueous/organic phase transfer promoter.

18. A process according to claim 10, wherein the amount of organic acid (d2) per mole of the compound of the $M^{n+}$ cation ranges from 0.25 to 1 mole per mole of $M_2O_n$.

19. A process according to claim 1, said organic acid (d2) comprising an aliphatic carboxylic acid, sulfonic or phosphoric acid, an alkylarylsulfonic acid or an alkylarylphosphonic acid.

20. A process according to claim 1, said organic liquid medium comprising an aliphatic or cycloaliphatic hydrocarbon, a chlorinated aromatic hydrocarbon, an aliphatic or cycloaliphatic ether, or an aliphatic or cycloaliphatic ketone.

* * * * *